(12) United States Patent
Fedynyshyn et al.

(10) Patent No.: US 11,845,219 B2
(45) Date of Patent: Dec. 19, 2023

(54) 3-D PRINTED DEVICES FORMED WITH MAGNETIC INKS AND METHODS OF MAKING GRADED INDEX STRUCTURES

(71) Applicants: Massachusetts Institute of Technology, Cambridge, MA (US); President and Fellows of Harvard College, Cambridge, MA (US)

(72) Inventors: Theodore H. Fedynyshyn, Sudbury, MA (US); Jennifer A. Lewis, Cambridge, MA (US); Bradley P. Duncan, Andover, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 517 days.

(21) Appl. No.: 16/864,522

(22) Filed: May 1, 2020

(65) Prior Publication Data

US 2020/0353682 A1    Nov. 12, 2020

Related U.S. Application Data

(60) Provisional application No. 62/843,935, filed on May 6, 2019.

(51) Int. Cl.
*B29C 64/00* (2017.01)
*B29C 64/165* (2017.01)
(Continued)

(52) U.S. Cl.
CPC ............ *B29C 64/165* (2017.08); *B05D 5/083* (2013.01); *B29C 64/209* (2017.08); *C09D 5/24* (2013.01);
(Continued)

(58) Field of Classification Search
CPC .......................... B29C 64/165; B29C 64/209
See application file for complete search history.

(56) References Cited

U.S. PATENT DOCUMENTS 7,485,366 B2    2/2009  Ma et al.
2008/0129462 A1*  6/2008  Vignola ............ G11B 33/0427
                                                      206/307
(Continued)

FOREIGN PATENT DOCUMENTS

CN        103756236 A    4/2014
CN        103980591 A    8/2014
(Continued)

OTHER PUBLICATIONS

Ho-Lung Li et al., A New Flexible and Multi-Purpose System Design for 3-Dimensional Printing, Proceedings of the ASME 2011 International Manufacturing Science and Engineering Conference, MSEC2011, Jun. 13-17, 2011, Corvallis, Oregon, USA, 7 pages.

(Continued)

*Primary Examiner* — Nicholas R Krasnow
(74) *Attorney, Agent, or Firm* — DALY, CROWLEY, MOFFORD & DURKEE, LLP

(57) ABSTRACT

A 3-D printed device comprising one or more structures, the structures comprising a plurality of magnetically responsive particles and one or more diblock or triblock copolymers; the diblock or triblock copolymers having an A-B, A-B-A, or A-B-C block-type structure in which the A-blocks and C-blocks are an aromatic-based polymer or an acrylate-based polymer and the B-blocks are an aliphatic-based polymer. These 3-D printed devices may be formed using a method that comprises providing a magnetic ink composition; applying the magnetic ink composition to a substrate in a 3-D solvent cast printing process to form one or more structures; and drying the one or more structures formed (Continued)

from the magnetic ink composition. The dried structures can exhibit one or more regions of magnetic permeability greater than $1.3 \times 10^{-6}$ H/m.

11 Claims, 5 Drawing Sheets

(51) Int. Cl.

| | |
|---|---|
| *B29C 64/209* | (2017.01) |
| *B05D 5/08* | (2006.01) |
| *C09D 5/24* | (2006.01) |
| *H01L 23/498* | (2006.01) |
| *H01B 1/00* | (2006.01) |
| *G03G 5/05* | (2006.01) |
| *G03G 5/07* | (2006.01) |
| *H01M 10/653* | (2014.01) |
| *H01M 4/66* | (2006.01) |
| *H05K 1/09* | (2006.01) |
| *B33Y 10/00* | (2015.01) |
| *B33Y 30/00* | (2015.01) |
| *B33Y 70/00* | (2020.01) |
| *B33Y 80/00* | (2015.01) |
| *B29K 23/00* | (2006.01) |
| *B29K 25/00* | (2006.01) |
| *B29K 105/00* | (2006.01) |
| *B29L 31/34* | (2006.01) |
| *G01N 33/00* | (2006.01) |

(52) U.S. Cl.
CPC ............... *G03G 5/05* (2013.01); *G03G 5/07* (2013.01); *H01B 1/00* (2013.01); *H01L 23/49883* (2013.01); *H01M 4/663* (2013.01); *H01M 10/653* (2015.04); *H05K 1/092* (2013.01); *B29K 2023/06* (2013.01); *B29K 2023/12* (2013.01); *B29K 2025/06* (2013.01); *B29K 2105/251* (2013.01); *B29K 2995/0006* (2013.01); *B29K 2995/0008* (2013.01); *B29K 2995/0088* (2013.01); *B29K 2995/0093* (2013.01); *B29K 2995/0094* (2013.01); *B29L 2031/3456* (2013.01); *B33Y 10/00* (2014.12); *B33Y 30/00* (2014.12); *B33Y 70/00* (2014.12); *B33Y 80/00* (2014.12); *G01N 2033/0095* (2013.01); *H05K 2201/015* (2013.01); *H05K 2201/03* (2013.01)

(56) References Cited

U.S. PATENT DOCUMENTS

| | | |
|---|---|---|
| 2012/0232206 A1 | 9/2012 | Wu et al. |
| 2013/0170171 A1 | 7/2013 | Wicker et al. |
| 2014/0176381 A1* | 6/2014 | Choi .................. H01Q 7/06 335/297 |
| 2014/0353862 A1 | 12/2014 | Erdman |
| 2015/0001762 A1 | 1/2015 | Lacaze et al. |
| 2015/0165675 A1 | 6/2015 | Dawson et al. |
| 2016/0120040 A1 | 4/2016 | Elmieh et al. |
| 2016/0122570 A1 | 5/2016 | Chae et al. |
| 2016/0263823 A1 | 9/2016 | Espiau et al. |
| 2016/0319122 A1 | 11/2016 | Niessner et al. |
| 2016/0346997 A1 | 12/2016 | Lewis et al. |
| 2017/0278603 A1* | 9/2017 | Moon ................ H01F 41/0253 |
| 2018/0205142 A1* | 7/2018 | Jung ........................ H01Q 1/38 |
| 2018/0218814 A1* | 8/2018 | Yoshida ................... C08K 3/08 |
| 2018/0230287 A1 | 8/2018 | Shiozawa |
| 2018/0236724 A1 | 8/2018 | Compton et al. |
| 2018/0320008 A1 | 11/2018 | Fedynyshyn et al. |
| 2019/0300741 A1 | 10/2019 | Duncan et al. |
| 2020/0328527 A1* | 10/2020 | Liu .......................... H01Q 3/30 |

FOREIGN PATENT DOCUMENTS

| | | |
|---|---|---|
| CN | 103980594 A | 8/2014 |
| CN | 103980672 A | 8/2014 |
| CN | 103980675 A | 8/2014 |
| CN | 104031304 A | 9/2014 |
| EP | 3412715 A1 | 12/2018 |
| JP | 3838730 B2 | 8/2006 |
| WO | 2014194155 A1 | 12/2014 |
| WO | 2014204450 A1 | 12/2014 |
| WO | 2015091814 A1 | 6/2015 |
| WO | 2016145309 A1 | 9/2016 |
| WO | 2017026420 A1 | 2/2017 |
| WO | 2017079130 A1 | 5/2017 |
| WO | 2019195117 A1 | 10/2019 |

OTHER PUBLICATIONS

Huang Bing et al., The Properties of an UV Curable Support Material Pre-Polymer for Three Dimensional Printing, Journal of Wuhan University of Technology-Mater, Sci. Ed., Apr. 2010, vol. 25, No. 2, DOI: 10.1007/s11595-010-2278-6, pp. 278-281.
International Search Report and Written Opinion, PCT/US2016/059858, dated Feb. 21, 2017, 10 pages.
International Search Report and Written Opinion, PCT/US2019/024941, dated Jul. 4, 2019, 8 pages.
Marc Behl et al., Shape-Memory Polymers, Center for Biomaterial Development, Institute of Polymer Research, Materials Today, Apr. 2007, vol. 10, No. 4, pp. 20-28.
Michael Lis et al., Polymer Dielectrics for 3D-Printed RF Devices in the Ka Band, Advanced Materials Technologies, DOI: 10.1002/admt.201600027, WILEY-VCH Verlag GmbH & Co. KGaA, 69469 Weinheim, Germany, 2016, 5 pages.
Michael Lis et al., Polymer Dielectrics for 3D-Printed RF Devices in the Ka Band, Advanced Materials Technologies, vol. 1, Issue 2 (May 6, 2016) pp. 1-6.
Milad Mirzaee et al., Developing Flexible 3D Printed Antenna Using Conductive ABS Materials, IEEE, Oct. 26, 2015, pp. 1308-1309.
International Preliminary Report on Patentability, PCT/US2020/031026, dated Nov. 18, 2021, 7 Pages.
U.S. Appl. No. 16/370,210, filed Mar. 29, 2019, Duncan, et al.
U.S. Appl. No. 15/773,282, filed May 3, 2018, Fedynyshyn, et al.
3D Printing Resolution, May 1, 2019, 3 space, https://3space.com/blog/what-does-resolution-mean-in-3d-printing/ (Year: 2019), pp. 10.
International Preliminary Report on Patentability, PCT/US2019/024941, dated Oct. 6, 2020, 6 Pages.
International Search Report and Written Opinion, PCT/US2020/031026, dated Jul. 17, 2020, 12 pages.
N,N-Dimethylformamide, Feb. 27, 2001, Sigma-Aldrich, https://www.signnaaldrich.com/content/dann/signna-aldrich/docs/Signna/Product Information Sheet/d4254pis.pdf (Year: 2001), pp. 1.
N,N-Dimethylformamide, 2015, PubChem, https://pubchem.ncbi.nlm.nih.gov/compound/N_N-Dimethylformamide (Year: 2015), pp. 77.

* cited by examiner

3-D PRINTED DEVICES FORMED WITH MAGNETIC INKS AND METHODS OF MAKING GRADED INDEX STRUCTURES

CROSS-REFERENCE TO RELATED APPLICATIONS

This application claims the benefit of U.S. Provisional Application Ser. No. 62/843,935, filed on May 6, 2019. The entire contents of the above-referenced provisional patent application is incorporated herein by reference.

FEDERALLY SPONSORED RESEARCH OR DEVELOPMENT

This invention was made with government support under contract number FA8702-15-D-0001 awarded by the U.S. Air Force. The government has certain rights in the invention.

FIELD

This disclosure relates generally to 3-dimensional (3-D) printed devices that contain at least one magnetically responsive component. The disclosure further relates to magnetically permeable ink compositions useful in a 3-D printing processes and methods of forming 3-D printed devices therefrom.

BACKGROUND

The statements in this section merely provide background information related to the present disclosure and may not constitute prior art.

Three-dimensional (3-D) printing is a process of making solid objects of virtually any shape from a digital model. In fact, 3-D printing is generally uses additive processes, i.e., where an object is created by depositing ("printing") successive layers of a material. In addition, 3-D printing is able to print more than one material at the same time. Thus, 3-D printing processes are able to build very complex many-layered structures direct from the design. Three-dimensional printing processes are routinely used for both rapid prototyping and manufacturing on demand. Several types of 3-D printing processes that may be used include ink jet printing, extrusion printing, laser/e-beam sintering, and laser/e-beam melting. Laser sintering and/or electron beam (e-beam) sintering are additive manufacturing techniques that use a laser or e-beam as a power source to sinter powdered metals into a 3-D printed shape by partial melting of the metal during contact with the laser or electron beam. The laser or e-beam may be directed to different locations in the powdered metal bed and when focused into a spot the exposed powder is sintered. Laser melting and/or electron beam melting are conceptually similar but instead of sintering the metal powder, the laser or e-beam imparts sufficient power into the powder to melt the metal and fuse it into a continuous mass thereby forming the metal powder into a solid 3-dimensional part. Both techniques can provide three-dimensional renderings of structure although at the increased expense associated with running a high temperature process that may also melt, damage, or decompose other structural components that are in close proximity.

Ink jet printing processes form 3-D structures by jetting a liquid binder onto a powder bed or a photopolymer through multiple jet heads followed by curing in order to fix or crosslink the deposited polymer. In order to use ink jet printing to form electronic devices, the process typically needs to be coupled with a sintering step. This sintering step generally involves exposing the deposited ink to high temperature heating (e.g., greater than 200° C.), light sintering, chemical sintering, or another sintering technique. This additional processing step adds to the manufacturing cost and increases process complexity. Thus, the use of an ink jet printing process is generally limited to the formation of simple features or structures that are capable of withstanding high temperatures.

Extrusion printing processes can be either thermal-based or solvent-based. A thermal-based extrusion 3-D printing process utilizes the extrusion of a thermoplastic material. This process works by melting a plastic filament that is deposited via a heated extruder, a layer at a time, onto a build platform according to 3-D spatial data supplied to the printer. Each layer hardens as it is deposited and bonds to the previous layer. Thus, an extrusion printing process is primarily a polymer-based printing technique and is not applicable to the printing of electronic devices.

SUMMARY

The present disclosure generally provides 3-D printed devices that contain one or more magnetically responsive regions, features or structures, as well as methods of forming such devices. The 3-D printed devices may be formed using a method that comprises providing a magnetic ink composition; applying the magnetic ink composition to a substrate in a 3-D solvent cast printing process to form one or more electronic structures (e.g., radiofrequency antennas); and drying the one or more structures formed from the ink composition.

In one aspect of the invention, 3-D printing inks are disclosed that are composed of at a minimum three components, a magnetically responsive particle, a block copolymer, and a solvent. One clear advantage of the invention is the ability to 3-D print magnetically responsive materials without the need for post-processing involving thermal, chemical, photolytic, or other sintering treatments.

Direct writing of polymeric materials requires inks that are capable of being extruded through a nozzle while maintaining shape once deposited. Highly concentrated solutions of polymers have been shown to exhibit highly shear thinning, a trait that provides low viscosity at the high shear rates typical of passing through a narrow nozzle under pressure and high viscosity at low shear rates as occurs when deposited. This shear thinning behavior allows the deposited polymer to hold its shape. This shape can be further stabilized through the rapid solvent evaporation or rapid photo-polymerization. After deposition, rapid evaporation of the solvent occurs further solidifying the printed object although solvent evaporation can occur at any time during and after deposition. Materials that exhibit high shear thinning typically have a near two orders of magnitude drop in viscosity going from low to high shear forces.

A material can be formulated containing a block copolymer and a solvent that can be used for 3-D printing of high resolution objects. These block copolymers can be employed as the only polymer in the system or can be used with other polymers for 3-D printing of high resolution objects. These polymers can be either diblock or triblock copolymers. When diblock copolymers are used they of the A-B type where A designates one type of polymer and B designates a second type of polymer. When triblock polymers are used they can be of the A-B-A type or the A-B—C type where A, B, and C designate a unique type of polymer.

Block copolymer can be particularly useful for 3-D printing when one of the blocks are selected from either polystyrene or a derivative of polystyrene and a second block is selected from either polyethylene, polypropylene, or a variant of a linear hydrocarbon polymer such as polybutadiene, polyisoprene, or poly(ethylene-ran-butylene) or a derivative of any of these polymers. These polymers have properties display sheer thinning behavior and as such are materials that can be deposited from solvent based extrusion 3-D printing.

Any molecular weight of the block copolymer can be employed in this invention. It is preferred that the molecular weight is between 10,000 and 10,000,000 Daltons and more preferred that the molecular weight be between 25,000 and 1,000,000 Daltons.

For triblock polymers, any monomer ratio of end block monomers to mid-block monomers is acceptable. It is preferred that the total "end block" block monomers be in the range of 10 to 50% and more preferred that the total end block block monomers be in the range of 15 to 30%.

The viscosity of the solution is a function of the polymer molecular weight and the amount of polymer dissolved in the solvent. Any combination of polymer molecular weight and the amount of polymer dissolved in the solvent is acceptable for this invention with a preferred amount of polymer dissolvent in the solvent to be greater than 5% or 10% and more preferred that the polymer dissolvent in the solvent to be greater than 25%.

In some embodiments of the invention a second polymer can be added to the block polymer solution and this second polymer can be a homopolymer, copolymer, terpolymer or higher polymer. The second polymer need not be a block copolymer to be useful for this invention and often a homopolymer or random copolymer can added to improve any properties of the 3-D printed object. Any polymer that is compatible with the block polymer can be employed in this invention without limitation. Any molecular weight of the block copolymer can be employed in this invention. In some instances, it is preferred that the molecular weight is between 10,000 and 10,000,000 Daltons or more preferred that the molecular weight be between 25,000 and 1,000,000 Daltons. Adding a second polymer allows for the modification of the printing ink and the final printed polymer through the use of mixtures of polymers and diblock or triblock polymers.

Non-limiting types of polymers that can be added to the block polymers are polyethylenes, polypropylenes, polytetrafluoroethylenes, polystyrenes, poly indenes, polyvinyl acetates, polyvinylalcohols, polyacrylates, polymethacrylates, polyacryonitrile, polyvinyl chloride, polyvinylidine chloride, polyamides, polyesters, epoxy resins, polyformaldehyde resins, amino-formaldehyde resins, phenol-formaldehyde resins, cellulose and cellulose derivatives, proteins, natural rubber, poly isoprene, polybutadiene, polynitrile rubbers, chloroprene rubbers, polyurethanes, and polysilicones.

These polymer-based inks display sheer thinning behavior and as such are materials that can be deposited from solvent-based extrusion 3-D printing. The printed polymers can be sufficiently stable in terms of holding their form as deposited. The polymers can also undergo as post-deposition stabilization process. One post-deposition stabilization process is to crosslink the polymers after or during deposition.

One method to perform this stabilization process would be to expose the polymers to actinic radiation of between 150 and 500 nm, with a preference to between 190 and 400 nm wavelengths. In some instances, the UV radiation by itself can be sufficient to allow the polymers to undergo crosslinking.

A second method would be to add either thermal or photo-induced free radical generator to the polymer to generate free radicals by either applying heat to the polymer or exposing the polymer to actinic radiation. Any number of known radical forming materials, such as photoinitiators, could find use in some implementations of this invention. Some examples of photoinitiators supplied by Ciba that would find use in this invention are Irgacure 184, Irgacure 261, Irgacure 369, Irgacure 379, Irgacure 500, Irgacure 651, Irgacure 727, Irgacure 750, Irgacure 784, Irgacure 819, Irgacure 907, Irgacure 1035, Irgacure 1700, Irgacure 1800, Irgacure 2959, Irgacure OXE01, Darocur 1173, Darocur 4265, Darocur TPO, Darocur BP, CGI 1905, and CGI 263. Any number of known radical forming materials, such as thermal radical generators can find use in some implementations of this invention. Some examples of thermal radical generators are 4,4-Azobis(4-cyanovaleric acid), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis(tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, Cumene hydroperoxide, Cyclohexanone peroxide, Dicumyl peroxide, Lauroyl peroxide, 2,4-Pentanedione peroxide, Peracetic acid, and Potassium persulfate.

In some embodiments one or more vinyl containing monomers can be as the solvent. One possible vinyl containing monomer would be styrene or divinyl styrene or a derivative of styrene or divinyl styrene, which can be employed with either a thermal or photo-induced free radical generator to crosslink the vinyl containing monomer in the presence of the polymer either during or after deposition.

A sensitizer can be added to the formulation to increase the absorbance of the material and, by energy transfer to the photo-initiator or photo-crosslinker, increase the amount of radicals generated and thus increase the sensitivity of the material toward photons. Any sensitizer can be chosen from those that are known in the art. Specific examples of sensitizers are UVS-1101, UVS-1221, and UVS-1331 from Kawasaki Kasei Chemcials Ltd.

A dye can be added to the formulation to increase the absorbance without sensitization of the material. Any dye that is added would be useful to produce a colored material that could be more aesthetically pleasing or offer other advantages. The dye can also absorb in the non-visible part of the spectrum and be employed to reduce the amount of light penetration in the material and thus limit the depth into the material of crosslinking. The advantage of limiting the depth can be a finer resolution in the depth or Z-direction of the voxel.

Non-limiting examples of magnetic particles that can be added to the formulated inks are iron carbonyl, yttrium iron garnet, and other ferrites.

In some instances, it can be preferred that the magnetically responsive particles be flat or plate-like in shape, in which the z-dimension is no more than 20% than of the x- or y-dimension and preferred to be no more than 10% than of the x- or y-dimension. The magnetic particles can be any size between 100 microns and 1 nanometer with a preferred size between 30 microns and 50 nanometers, and a most preferred side between, 15 microns and 100 nanometers.

The magnetic particles may be added directly to the ink or the surface of the particles may be modified to increase compatibility with the ink. One method to increase compatibility is to increase of hydrophobicity of the particle. This can be accomplished by attaching a hydrophobic moiety to the surface of the particle through either covalent attachment or ionic attachment or any other means of surface absorption.

The magnetic particle surface can also be modified by employing polymers such as polyvinylpyrrolidone. A second method to modify the particle surface is by employing ester containing compounds such as aluminum sterate. A third method to modify the surface is by employing silane coupling agents such as chlorosilanes or alkoxysilanes. A fourth method to modify the surface is by employing surfactants such as steric acid or lauryl acid. A fifth method is to employ thiol-containing organics. Those skilled in the art will recognize that other methods that modify the particle surface to increase solvent and ink compatibility may also be employed.

The invention covers 3-D printing inks consisting of magnetic particles and block polymers specifically diblock and triblock polymers and more specifically triblock copolymers. Not to be bound by theory the triblock copolymers must have end-blocks and mid-blocks are completely incompatible polymers such that if a mixture of the two polymers would undergo phase separation. In a block copolymer these incompatible phases are chemically bonded together and cannot separate but instead arrange themselves into domains on a microscopic level. The end-blocks can attach to other end-blocks, effectively crosslinking the diblock copolymer and leading to a highly viscous solution which can undergo sheer thinning when the sheer force disrupts that crosslinking leading to a lowering of solution viscosity and enhanced flow.

Any two incompatible polymers can be used in the triblock copolymer. It is preferred that one block contain an aromatic or acrylate-based monomer and the second block contain an aliphatic based monomer. Styrene or any substituted styrene would make an acceptable aromatic portion of the block polymer. Any acrylate or methacrylate-based monomer would also make an acceptable monomer for one on the blocks of the block polymer. Any aliphatic based monomer or substituted aliphatic based monomer would make an acceptable monomer for one on the blocks of the block polymer including polybutadiene, polyisoprene, or poly(ethylene-ran-butylene) or a derivative of any of these polymers.

Any solvent can be employed in this invention as long as the solvent is capable of solubilizing the block polymer as well as any added polymers. Preferred solvents are benzene, toluene, xylene, ethyl benzene, styrene, tetralin, or any other substituted aromatic solvent. Other solvents can be a cellosolve type solvent such as methyl cellosolve, ethyl cellosolve, methyl cellosolve acetate or ethyl cellosolve acetate. Ethylene glycol-based solvents such as ethylene glycol monomethyl ether, diethylene glycol monomethyl ether, diethylene glycol dibutyl ether, diethylene glycol and diethylene glycol dimethyl ether are also suitable as organic solvents for ink compositions. Further, propylene glycol based solvents such as propylene glycol monoethyl ether, propylene glycol monobutyl ether, propylene glycol monomethyl ether acetate, dipropylene glycol dimethyl ether or propylene glycol monoethyl ether acetate can be used. Suitable ester type solvents include butyl acetate, amyl acetate, ethyl butyrate, butyl butyrate, diethyl oxalate, ethyl pyruvate, ethyl-2-hydroxybutyrate, 2-methylacetoacetate, methyl lactate or ethyl lactate. Alternatively, alcohols are utilized and include heptanol, hexanol, nonanol, diacetone alcohol or furfuryl alcohol. Examples of suitable ketone solvents include cyclohexanone or methyl amyl ketone. Ethers useful as solvating agents include methyl phenyl ether or diethylene glycol dimethyl ether. Polar solvents, such as dimethylformamide or N-methylpyrrolidone can also be used. A solvent can be used alone or as combinations of two or more solvents. The solvent is typically used in an amount of from 1 to 100 times by weight relative to the total amount of the solid content of the ink composition.

Further, the ink compositions consistent with embodiments of the present invention can contain various additives such as a surfactant, a coating property-improving agent, a stabilizer, a colorant and an ultraviolet absorber, to such an extent as not to impair the desired properties.

Suitable surfactants which can be added to an ink composition to improve its coating ability include, for example, nonionic surfactants. Such nonionic surfactants can include polyoxyethylene alkyl ethers such as polyoxyethylene lauryl ether, polyoxyethylene stearyl ether and polyoxyethylene oleyl ether, polyoxyethylene alkylphenyl ethers such as polyoxyethylene octylphenyl ether and polyoxyethylene nonylphenyl ethers. Further, suitable nonionic ester surfactants include polyethylene glycol dialkyl esters, such as polyethylene glycol dilaurate and polyethylene glycol distearate. Alternatively, fluorine-containing surfactants can be utilized which contain a fluoroalkyl or perfluoroalkyl group such as Efftop EF301, EF303 and EF352 (manufactured by Shinakitakasei Co., Ltd., Japan), Megafac F171, F172 and F173 (manufactured by Dainippon Ink Co., Ltd., Tokyo, Japan), Asahiguard AG710 (manufactured by Asahi Glass Co., Ltd., Japan), Florade FC430 and FC431 (manufactured by Sumitomo 3M Co., Ltd., Japan), and Surflone S-382, SC101, SC102, SC103, SC104, SC105 and SC106 (manufactured by Asahi Glass Co., Ltd., Japan). Organosiloxane surfactants, such as organosiloxane polymer KP341 (manufactured by Shinetsu Kagaku Kogyo Co., Ltd., Japan) are also suitable for decreasing the surface tension of the solution containing the photosensitive composition. Additionally, acrylic acid- or methacrylic acid-type polymers and copolymers such as Polyflow No. 75, No. 95 and WS (manufactured by Kyoeisha Yushikagaku Kogyo Co., Ltd., Japan); and the like are also suitable surfactants. The surfactant can be added to in an amount of less than about 2 parts by weight per 100 parts per weight of the coating composition. In one embodiment, surfactant can be added in an amount of about 0.005 to about 1 part by weight per 100 parts by weight. Furthermore, antioxidants or defoaming agents can be included in a composition as desired to attenuate the ink composition.

In certain embodiments, the invention is particularly useful in constructing low loss (or high gain) electronic structures, such as wideband horn antennas (4-50 GHz). For example, the inventive techniques disclosed herein can be used to construct a single wideband conformal antenna that can replace several conventional antennas. More generally, the invention facilitates construction of devices that can control propagation of electromagnetic waves by providing graded index (GRIN) material transition regions, e.g., regions of the variable permittivity and/or permeability.

The ink compositions generally comprise a plurality of magnetically responsive particles dispersed in a solvent along with one or more solubilized diblock or triblock copolymers. These diblock or triblock copolymers have an A-B, A-B-A, or A-B-C block-type structure in which the A-blocks and C-blocks are an aromatic-based polymer or an acrylate-based polymer and the B-block is an aliphatic-based polymer.

Although the use of diblock and/or triblock copolymers in 3-D printing processes has been known, it was generally assumed that such polymeric carriers could not be mixed with sufficient amounts of magnetically responsive fillers to yield useful features. Surprisingly, the polymeric carriers of the present invention are able to support large quantities of magnetically responsive filler materials while still maintaining sufficient fluidity to permit 3-D printing of conductive features. The high permeability inks of the present invention can also be used without the need for any thermal post-printing step to remove or reduce the amount of polymer in the formed features. For example, the drying step can be conducted at a temperature that is less than 200° C., or less than 100° C., or in some instances even at room temperature.

In one aspect of the invention, methods of forming a 3-D printed devices are disclosed utilizing a magnetic ink composition comprising a plurality of magnetically responsive particles dispersed in a solvent along with one or more solubilized diblock or triblock copolymers; the diblock or triblock copolymers having an A-B, A-B-A, or A-B-C block-type structure in which the A-blocks and C-blocks are an aromatic-based polymer or an acrylate-based polymer and the B-blocks are an aliphatic-based polymer. In these methods, the magnetic ink composition is applied to a substrate in a 3-D solvent cast printing process; and then dried to form the one or more structures formed from the magnetic ink composition, wherein the dried structures exhibit a magnetic permeability greater than about $1.3 \times 10^{-6}$ H/m.

Generally speaking, the magnetically responsive particles of the ink compositions can comprise from about 0.5% wt. % to about 95% wt. %, or preferably at least 20 wt. %, or least 30 wt. %, or at least 40 wt. %, or at least 50 wt. %, or least 60 wt. %, or at least 70 wt. %, or at least 80 wt. %, or least 90 wt. %, of at least a portion of the structure based on the dry weight of the applied ink composition. In certain embodiments, the magnetic ink compositions comprise 60 wt. % or more of the magnetically responsive particles, 20 wt. % or less of the one or more the diblock or triblock copolymers, and less than 25 wt. % of the solvent-based upon the overall weight of the ink composition. In other embodiments, the magnetic ink composition comprises 75 wt. % or more of the magnetically responsive particles, 15 wt. % or less of the one or more the diblock or triblock copolymers, and less than 15 wt. % of the solvent-based upon the overall weight of the ink composition. In other embodiments, the magnetic ink composition comprises 85 wt. % or more of the magnetically responsive particles, 10 wt. % or less of the one or more the diblock or triblock copolymers, and less than 10 wt. % of the solvent-based upon the overall weight of the ink composition. In some instances, the preferred weight percentage of magnetically responsive particles in the magnetic ink compositions ranges from about 20% to about 95%, or from 40% to 90%, or from 50% to 85%.

The magnetically responsive particles can have an average particle size in an x-dimension or y-dimension or z-direction that is in the range of about 10 nanometers to about 15 micrometers. In some embodiments, the particles can be roughly spherical in shape, or elongated in one dimension. In other embodiments, the particles can have a flattened or disc-like shape, e.g., have an aspect ratio defined by lengths in the x-, y-, and z-dimensions, such that the magnetically responsive particles have a z-dimension that is no more than 20% of the lesser of the x-dimension or the y-dimension.

In certain embodiments, the magnetically responsive particles in the ink composition can include one or more of the following: iron, nickel, cobalt or manganese, or oxides and carbonyls of such metals or their alloys, or mixtures thereof. In some embodiments, ferrite nanoparticles can be advantageous, including for example, spinel ferrites (e.g., $ZnFe_2O_4$), hexagonal ferrites (e.g., $BaMe_2Fe_2O_{12}$) and garnet ferrites (e.g., $Y_3Fe_5O_{12}$). In other embodiments, the magnetically responsive particles can be manganites, such as $La_xSr_{1-x}MnO_3$. Particles such as FeBNd or SmCo can also be used.

The magnetically responsive particles can also have a surface that is modified with a hydrophobic moiety, polyvinylpyrrolidone, an amine-containing compound, or a silane coupling agent. The solvent can also include a curable vinyl-containing monomer or mixture of vinyl-containing monomers.

The magnetic ink composition can further include a thermal or photo-induced free radical generator, and the process further comprises subjecting the deposited structure to sufficient heat or actinic radiation to generate the free radicals. The magnetic ink composition can also include at least one of a sensitizer, a dye, a surfactant, a stabilizer, a colorant, an ultraviolet absorber, an antioxidant, or a defoaming agent.

The magnetic ink compositions of the present invention can further include one or more dielectric materials having a different electrical permittivity than the magnetically responsive materials.

In another aspect of the invention, 3-D printed devices are disclosed having one or more structures, the structures including a plurality of magnetically responsive particles and one or more diblock or triblock copolymers; the diblock or triblock copolymers having an A-B, A-B-A, or A-B-C block-type structure in which the A-blocks and C-blocks are an aromatic-based polymer or an acrylate-based polymer and the B-blocks are an aliphatic-based polymer. In some embodiments, the structures exhibit a magnetic permeability equal to or greater than about $1.3 \times 10^{-6}$ H/m or exceed $1 \times 10^{-6}$ H/m without being subjected to a post-processing sintering treatment and/or the structures can also exhibit a printing resolution of less than 1,600 micrometers (μm).

The 3-D devices of the invention can exhibit differential permeability, e.g., different regions of the can be made more or less magnetically permeable by varying the concentration of the magnetically responsive particles in the ink composition as the device is being formed. Moreover, the devices can be made both magnetically responsive and dielectric particles and different ratios of dielectric and magnetically responsive materials can be useful in fine tuning "graded index" devices, e.g., devices in which the permeability and/or permittivity changes from on region of the device to another. Variations in the permeability and/or permittivity can be particularly useful in RF devices, such as antennas where "impedance matching" is desirable.

The 3-D printed devices according to the invention can include low size weight and power (SWaP) devices, microfluidic devices, biocompatible medical devices, or digital phased arrays that includes a mixture of digital and RF functions.

Further areas of applicability will become apparent from the description provided herein. It should be understood that the description and specific examples are intended for pur-

DETAILED DESCRIPTION

Figure 1:
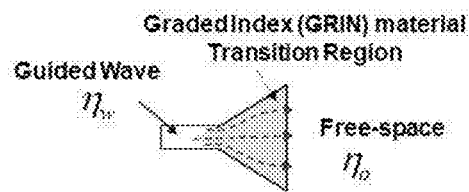
FIG. 1 is a schematic illustration of an RF waveguide coupled at its output aperture to an RF horn antenna of graded-index material that can be 3-D printed according to the invention.

The following description is merely exemplary in nature and is in no way intended to limit the present disclosure or its application or uses. For example, the 3-dimensional (3-D) printed devices made and used according to the teachings contained herein are described throughout the present disclosure in conjunction with radio frequency (RF) devices in order to more fully illustrate the composition and the use thereof. The incorporation and use of such structures formed according to the teachings of the present disclosure in other devices, including, but not limited to, low size weight and power (SWaP) devices, microfluidic devices, biocompatible medical devices, or digital phased arrays that include a mixture of digital and RF functions, or the like are contemplated to be within the scope of the present disclosure.

The present disclosure uses a 3-D printing process to deposit a magnetic ink in order to form advanced devices that offer significant advantages in properties or performance over commercially available materials or allow for the fabrication of devices not possible by conventional fabrication methods. The 3-D printed devices comprise one or more structures that exhibit a magnetic permeability greater than about $1.3 \times 10^{-6}$ H/m or more preferably in some instances greater than $1 \times 10^{-5}$ H/m.

The ability to print these magnetic inks using a high resolution 3-D printing process enables one to form any number of advanced devices, including without limitation fully integrated MHz to THz RF devices, flexible electronics, and microfluidics. The use of a high resolution, 3-D printing process offers significant intrinsic advantages for enhancing device performance and reducing SWaP. These advantages are based on the fact that devices can fabricated by 3-D printing according to the present disclosure with a resolution capability that subtractive manufacturing cannot typically achieve. A major limiting factor for the 3-D printing of high frequency devices is the availability of printable materials for magnetic features that exhibit good RF properties and that do not require high temperature post-processing, which can damage or decompose organic dielectrics.

According to one aspect of the present disclosure, the 3-D printing of the magnetic inks provides for the formation of high resolution structures, e.g., components or structures are printed in close proximity to each other, with some regions exhibiting permeability and other regions exhibiting dielectric properties or providing a graded variation in such properties. This ability may be important for many applications that are focused on the miniaturization of devices. One such example is a device where many different types of functionality are placed in a small volume or area such as horn antennas, phase array antennas and, more generally, in low size weight and power (SWaP) devices.

One advantage of the present disclosure is the ability to 3-D print magnetically responsive materials without the need for heating, sintering or other post-processing treatments that involve thermal sintering, chemical sintering, photolytic sintering, or any other type of high temperature heat treatment. Thus, the use of the 3-D printable magnetic inks allows for easy manufacturing, reproduction, and use of these devices by making it straight forward to go from design to a physical part using a 3-D printing process. In other words, the use of a simplified manufacturing process for multilevel and complex devices will accelerate the design-to-test cycle and enhance the pace of innovation with extensions into full manufacturing.

For the purpose of this disclosure the terms "about" and "substantially" are used herein with respect to measurable values and ranges due to expected variations known to those skilled in the art (e.g., limitations and variability in measurements). Typically, the term "about" encompasses deviations in a value of about +1-10%, or +1-5%.

As used herein, the term "polymer" refers to a molecule having polymerized units of one or more species of monomer. The term "polymer" is understood to include both homopolymers and copolymers. The term "copolymer" refers to a polymer having polymerized units of two or more species of monomers, and is understood to include terpolymers. As used herein, reference to "a" polymer or other chemical compound refers one or more molecules of the polymer or chemical compound, rather than being limited to a single molecule of the polymer or chemical compound. Furthermore, the one or more molecules may or may not be identical, so long as they fall under the category of the chemical compound. Thus, for example, "a" polyurethane may be interpreted to include one or more polymer molecules of the polyurethane, where the polymer molecules may or may not be identical (e.g., different molecular weights).

For the purpose of this disclosure, the term "weight" refers to a mass value, such as having the units of grams, kilograms, and the like. Further, the recitations of numerical ranges by endpoints include the endpoints and all numbers within that numerical range. For example, a concentration ranging from 40% by weight to 60% by weight includes concentrations of 40% by weight, 60% by weight, and all concentrations there between (e.g., 40.1%, 41%, 45%, 50%, 52.5%, 55%, 59%, etcetera).

For the purpose of this disclosure, the terms "at least one" and "one or more of" an element are used interchangeably and may have the same meaning. These terms, which refer to the inclusion of a single element or a plurality of the elements, may also be represented by the suffix "(s)" at the end of the element. For example, "at least one polyurethane", "one or more polyurethanes", and "polyurethane(s)" may be used interchangeably and are intended to have the same meaning.

The term "magnetically responsive" as used herein (e.g., with reference to the particles contained in the magnetic ink compositions) is intended to encompass materials that exhibit a magnetic permeability greater than about $1.3 \times 10^{-6}$ H/m or greater than about $1 \times 10^{-5}$ H/m The term "dielectric" as used herein is intended to encompass materials that exhibit high permittivity. Permittivity is a measure of a material's ability to store an electric field in the polarization of a medium. Dielectric materials typically have a dielectric constant greater than 2 and exhibit little to no conductivity.

The term "graded index" as used herein is intended to encompass structures that exhibit variations in their magnetic (and/or electrical) properties, e.g., having regions exhibiting different permeability or permittivity (or both). The variations need not be defined by a linear gradient but rather can also encompass exponential gradients as well as gradients defined by higher order functions. Graded index devices can be particularly useful in RF antennas to provide better impedance matching between an RF waveguide and free space conditions.

The term "nanoparticle" as used herein refers to particles having an average size in at least one dimension (X, Y, or Z) between about 1 nanometer and 1000 nanometers, preferably in some instances below 1000 nanometers or below 500 nanometers.

The magnetic ink compositions of the present disclosure are composed of at least three components, namely, a plurality of magnetically responsive particles, one or more block copolymers, and a solvent. One advantage of incorporating a sufficient concentration of magnetically responsive particles in the ink composition is that the ink composition exhibits magnetic permeability when printed on a substrate and dried without the need for post-processing treatment. The amount of magnetically responsive particles in the ink composition may be greater than 10% or 20% or 30% or 40 wt. % of the total weight of the ink including the copolymer and solvent. Alternatively, the amount of magnetically responsive particles may be greater than 60 wt. % of the total weight of the ink; alternatively, the amount of magnetically responsive particles may be greater than 75 wt. % of the total weight of the ink.

The amount of block copolymers incorporated into the ink composition should impart sheer thinning behavior to the ink without reducing the permeability of the ink. The amount of block copolymers may be less than 30% or 20 wt. % of the total weight of the ink including the magnetically responsive particles and solvent. Alternatively, the amount of block copolymers may be less than 15 wt. % of the total weight of the ink. Alternatively, the amount of block copolymers may be less than 10 wt. % of the total weight of the ink.

The amount of solvent present in the ink composition also imparts sheer thinning behavior to the ink but not so much as to reduce the viscosity of the ink to levels at which sheer thinning behavior is diminished or Newtonian behavior is encountered. The amount of solvent may be less than 75% or 60% or 50% or 25 wt. % of the total weight of the ink including the metal and block copolymers. Alternatively, the amount of solvent may be less than 15 wt. % of the total weight of the ink. Alternatively, the amount of solvent may be less than 10 wt. % of the total weight of the ink.

Block Copolymers—

The block copolymers can be employed as the only polymer in the magnetic ink composition or when desirable used with other polymers to form high resolution structures in a 3-D printing process. These block copolymers can be either diblock or triblock copolymers; alternatively, the block copolymers are triblock copolymers. When diblock copolymers are used they may have an A-B block-type structure where A-blocks designates one type of polymer and B-blocks designate a second type of polymer. When triblock copolymers are used they may have an A-B-A block-type or an A-B-C block-type structure, where A-blocks, B-blocks, and C-blocks designate different polymers.

The block copolymers must have end-blocks (e.g., A-blocks and C-blocks) and mid-blocks (e.g., B-blocks) that are incompatible polymers, such that if a simple mixture of the two polymers would undergo phase separation. However, in the block copolymers these incompatible phases are chemically bonded together and cannot separate but instead arrange themselves into domains on a microscopic level. Although not wanting to be strictly held to theory, the end-blocks of the copolymers may become attracted to end-blocks in adjacent copolymers, thereby, leading to the formation of a highly viscous solution. However, this viscous polymer solution will undergo shear thinning when the shear force disrupts the attractive forces, thereby, lowering the solution viscosity and enhancing the ability to copolymers to flow.

Any two incompatible polymers can be used in formation of the block copolymers. When desirable, end-blocks (e.g., A-blocks and C-blocks) may comprise an aromatic-based or acrylate-based polymer and the mid-blocks (e.g., B-blocks) may comprise an aliphatic-based polymer. According to one aspect of the present disclosure, the use of styrene or any substituted styrene is acceptable for the aromatic portion of the block copolymers. Any acrylate-based or methacrylate-based polymer is also acceptable for use as one of the A-blocks or C-blocks of the block copolymers. Any aliphatic-based polymer or substituted aliphatic-based polymer is acceptable for use as the B-blocks in the block copolymers. Alternatively, the A-blocks and C-blocks in the diblock and/or triblock copolymers may be selected from either polystyrene or a derivative of polystyrene and a B-blocks are selected from either polyethylene, polypropylene, or a variant of a linear hydrocarbon polymer, such as polybutadiene, polyisoprene, or poly(ethylene-ran-butylene), or a derivative of any of these polymers. The copolymers having the A-, B-, and C-blocks as defined herein exhibit sheer thinning behavior and as such are materials that may be deposited using either a melt-based or solvent-based extrusion 3-D printing process.

Any molecular weight of the block copolymers can be used in the magnetic ink composition of the present disclosure. Alternatively, the molecular weight of the diblock and/or triblock copolymers used in the magnetic ink is between about 10,000 and 10,000,000 Daltons; alternatively, between about 25,000 and 1,000,000 Daltons.

Similarly, any ratio of end-block polymers (e.g., A-blocks and C-blocks) to mid-block polymers (e.g., B-blocks) is acceptable for use in the magnetic ink composition of the present disclosure. Alternatively, the ratio of A-blocks and C-blocks to B-blocks in the diblock or triblock copolymers is in the range of about 1:1 and 1:10; alternatively, in the range of about 3:20 and 3:10.

The viscosity of the magnetic ink composition is a function of the molecular weight of the block copolymers and the amount of copolymer that is dissolved in the solvent. Any combination of copolymer molecular weight and the amount of copolymer dissolved in the solvent is acceptable for use in the magnetic ink of the present disclosure. The amount of polymer dissolved in the solvent may be greater than 5% or 10 wt. %; or alternatively, greater than 25 wt. % based on the overall weight of the magnetic ink composition.

When desirable, a second or additional polymer may be added to the magnetic ink composition. This second or additional polymer may be a homopolymer, copolymer, terpolymer or higher polymer. The second polymer need not be a block copolymer to be used with the block copolymer in the magnetic ink. Rather, a homopolymer or random copolymer can added to improve one or more properties exhibited by the 3-D printed structure or feature. This second or additional polymer should be compatible with the block copolymer present in the magnetic ink composition. The addition of this second polymer to the magnetic ink composition allows for the modification of the properties exhibited by the printing ink and the final printed structure through the use of mixtures of polymers and block copolymers.

Several non-limiting examples of the second polymers that can be added to the magnetic ink composition and used in conjunction with the block copolymers are polyethylenes, polypropylenes, polytetrafluoroethylenes, polystyrenes, poly indenes, polyvinyl acetates, polyvinylalcohols, polyacrylates, polymethacrylates, polyacryonitrile, polyvinyl chloride, polyvinylidine chloride, polyamides, polyesters, epoxy resins, polyformaldehyde resins, amino-formaldehyde resins, phenol-formaldehyde resins, cellulose and cellulose derivatives, proteins, natural rubber, polyisoprene, polybutadiene, polynitrile rubbers, chloroprene rubbers, polyurethanes, and polysilicones.

Magnetically Responsive Particles—

The magnetically responsive particles may comprise, without limitation particles of iron, nickel, cobalt and manganese, or oxides and carbonyls of such metals, as well as alloys and mixtures thereof. The magnetic particles are incorporated into the magnetic ink formulation in an amount that does not interfere with the 3-D printing process. The magnetically responsive particle's geometry may be a flake, sphere, cube, rod, wire, or any irregular shape.

Several examples of magnetically responsive particles that can be used in the magnetic ink compositions can include one or more of the following: iron, nickel, cobalt or manganese, or oxides and carbonyls of such metals or their alloys, or mixtures thereof. In some embodiments, ferrite nanoparticles can be advantageous, including for example, spinel ferrites (e.g., $ZnFe_2O_4$), hexagonal ferrites (e.g., $BaMe_2Fe_2O_{12}$) and garnet ferrites (e.g., $Y_3Fe_5O_{12}$). In other embodiments, the magnetically responsive particles can be manganites, such as $La_xSr_{1-x}MnO_3$. Particles such as FeBNd or SmCo may also be used.

More generally, magnetically responsive particles according to the invention can include transition metals such as Fe, Co, Ni, Mn, and Zn; transition metal intermetallic alloys such as Fe—Ni, Fe—Co, Co—Ni, Fe—B, Fe—N, Fe—Zr, Fe—Si, Fe—Si—B, Fe—Zr—B, Fe—P—B, Mn—Zn, and Ni-Zn; and transition metal-rare earth alloys, such as Fe—Nb, Fe—Sm, as well as oxides and carbonyls of such metals or alloys or mixtures thereof.

Additional information on magnetically responsive materials can be found in U.S. Pat. No. 7,485,366 and Japanese Patent No. 3,838,730, both of which are herein incorporated by reference in their entireties.

The magnetically responsive particles may be of any shape including spherical, flat, polyhedron, or irregular. Alternatively, the magnetically responsive particles may be characterized as having an aspect ratio defined by lengths in the x-, y-, and z-dimensions, such that the magnetically responsive particles have a z-dimension that is no more than 20% of the lesser of the x-dimension or the y-dimension; alternatively, less than 10% of the x-dimension or the y-dimension. When desirable, the magnetically responsive particles may be described as being flat. The magnetically responsive particles may also be characterized as having a particle size in the x-dimension and/or y-dimension that is in the range of about 0.1 micrometer ($\mu m$) to about 15 micrometers; alternatively, in the range of about 2 micrometers to about 8 micrometers; alternatively, in the range of about 2 micrometers to about 4 micrometers; alternatively, in the range of about 0.1 $\mu m$ to about 2 $\mu m$.

The magnetically responsive particles may be added directly to the block copolymers and solvent in the ink composition or alternatively, the surface of the particles may be modified to increase compatibility with the block copolymers and solvent. One method of increasing such compatibility is to enhance the hydrophobicity of the particle's surface. In this respect, one may attach a hydrophobic moiety to the surface of the particle through covalent bonding, ionic attraction, or any other known surface absorption technique. Several examples, of polymers and compounds that may be used to modify the surface of the particles, include but are not limited to polyvinylpyrrolidone; amine-containing compounds, such as decylamine; silane coupling agents, such as chlorosilanes and/or alkoxysilanes; surfactants, such as steric acid or lauryl acid; and thiol-containing organic compounds. Those skilled in the art will recognize that other methods of modifying the particle's surface in order to increase solvent and ink compatibility may be used without exceeding the scope of the present disclosure.

Dielectric Particles—

As noted above, electrically polarizable (dielectric) particles may also be added to the ink formulation in any amount that does not interfere with printing and/or undesirably limit the magnetic properties of the structure. The incorporation of dielectric filler particles can be useful in impedance matching applications.

In certain embodiments, the dielectric particles having a low RF loss. Preferred dielectric particles exhibit a dielectric constant greater than about 2 and may be selected from the following: aluminum oxide, boron nitride, beryllium oxide, magnesium oxide, magnesium titanate, titanium dioxide, strontium titanate, barium titanate, molybdenum sulfide, zinc oxide, magnesium carbonate, borosilicate glass, mica, sapphire, fused silica, fused quartz, steatite, soda-line glass, zirconia, and wollastonite. The dielectric particles used in the exemplary ink formulations described below include magnesium oxide, aluminum oxide, titanium dioxide or strontium titanate.

Other suitable dielectric particles can include aluminum nitride, antimony oxide, barium oxide, barium carbonate, boron silicide, bismuth oxide, cadmium sulfide, calcium carbonate, cerium oxide, calcium boride, copper oxide, copper sulfide, cobalt oxide, chromium carbide, chromium nitride, dysprosium oxide, europium oxide, iron oxide, indium oxide, indium tin oxide, hafnium oxide, hafnium carbide, hafnium boride, hafnium silicide, gadolinium oxide, lanthanum oxide, lanthanum boride, lanthanum fluoride, manganese oxide, manganese carbonate, manganese nitride, molybdenum oxide, molybdenum carbide, molybdenum sulfide, neodymium oxide, niobium carbide, nickel oxide, praseodymium oxide, silicon dioxide, titanium oxide, titanium silicide, titanium nitride, titanium boride, tin oxide, terbium oxide, tungsten carbide, tungsten oxide, tungsten sulfide, tantalum carbide, silicon carbide, silicon nitride, strontium carbonate, yttrium oxide, vanadium carbide, zinc carbonate, zinc oxide, zirconium boride, zirconium carbide, zirconium sulfide, zirconium silicide, zirconium nitride, zirconium oxide, carbon black and/or talc. It is well know that metal oxides can exist with different oxidation states of the metal and all oxidation states of the metal may be suitable.

The dielectric particles can have an average particle size in the range from about 1 nm to about 10 microns or more typically in the range from about 1 nm to about 1000 nm. Thus, the dielectric particles may be referred to as nanoparticles. The average particle size may be understood to refer to an average primary particle size or crystallite size. The average size of the dielectric particles may be determined using any of the number of characterization techniques known in the art, such as x-ray diffraction or transmission electron microscopy. The surfaces of such dielectric particles can be modified in the same ways as the magnetically responsive particles (can be as discussed above).

Additional information on the use of dielectric particles in ink jet printing processes can be found in U.S. Published Patent Application No. 2018/0320008 entitled "Block Copolymer Ink Formulation For 3-D Printing And Method Of Making A 3-D Printed Radiofrequency (RF) Device" herein incorporated by reference in its entirety.

Solvents—

Any type of solvent may be used in the magnetic inks of the present disclosure as long as the solvent is capable of solubilizing the block copolymers, as well as any optionally added or secondary polymers. The solvent in the magnetic ink composition may comprise an aromatic solvent, a cellosolve-based solvent, a glycol-based solvent, an ester-based solvent, a ketone-based solvent, an alcohol-based solvent, an ether-based solvent, a highly polar solvent, or a mixture or combination thereof. Alternatively, the solvent has a boiling point that is in the range of about 80° C. to 220° C.

Several examples of aromatic solvents include but are not limited to benzene, toluene, xylene, ethylbenzene, tetralin, cumene (isopropylbenzene), cymene (isopropyltoluene), chlorobenzene, dichlorobenzene, mesitylene, or any other substituted aromatic solvent. Several examples of cellosolve-based solvent include, without limitation methyl cellosolve, ethyl cellosolve, methyl cellosolve acetate or ethyl cellosolve acetate. Several examples of glycol-based solvents, include but are not limited to ethylene glycol monomethyl ether, diethylene glycol monomethyl ether, diethylene glycol dibutyl ether, diethylene glycol, diethylene glycol dimethyl, propylene glycol monoethyl ether, propylene glycol monobutyl ether, propylene glycol monomethyl ether acetate, dipropylene glycol dimethyl ether, or propylene glycol monoethyl ether acetate.

Several non-limiting examples of ester-based solvents include butyl acetate, amyl acetate, ethyl butyrate, butyl butyrate, diethyl oxalate, ethyl pyruvate, ethyl-2-hydroxybutyrate, 2-methylacetoacetate, methyl lactate, or ethyl lactate. The alcohol-based solvents may include, without limitation, heptanol, hexanol, nonanol, diacetone alcohol, or furfuryl alcohol.

Several examples of suitable ketone-based solvents include but are not limited to cyclohexanone or methylamyl ketone. Several non-limiting examples of ether-based solvents that are useful as solvating agents include methyl phenyl ether and diethylene glycol dimethyl ether. The polar solvents that may be used in the ink composition include, but are not limited to dimethylformamide and N-methylpyrrolidone.

Each solvent can be used in the magnetic ink composition either alone or as a combination of two or more solvents. The solvent is typically present in an amount that ranges from 1 to 100 times by weight relative to the total amount of the solid content of the ink composition.

The printed magnetic ink may be sufficiently stable in terms of holding their form or shape as deposited. However, according to another aspect of the present disclosure, the printed copolymers may be subjected to or undergo a post-deposition stabilization process. One such post-deposition stabilization process would be to crosslink the copolymers after or during deposition. This type of stabilization process may include exposing the printed ink composition to actinic radiation having a wavelength that is between about 150 and about 500 nm; alternatively, in the wavelength range from about 190 nm to about 400 nm. The use of such ultraviolet (UV) radiation by may be sufficient to allow the copolymers to undergo crosslinking.

Solvent evaporation may lead to anisotropic shrinkage, particularly in the case of thicker (e.g., multilayer) printed structures or bodies. To ameliorate these effects, the aromatic solvents may be replaced with a curable vinyl-containing monomer or mixture of vinyl-containing monomers. The replacement of the aromatic solvents with the vinyl-containing monomers does not have a detrimental effect on the rheological properties exhibited by the ink composition. In some cases, the solvent may comprise a vinyl-containing monomer selected from among 4-benzhydrylstyrene, 4-tert-butylstyrene, 2,4-dimethylstyrene, 2,5-dimethylstyrene, 2,4-diphenyl-4-methyl-1-pentene, 2-methylstyrene, 3-methylstyrene, 4-methylstyrene, a-methylstyrene, 2,3,4,5,6-pentafluorostyrene, styrene, 2,4,6-trimethylstyrene, 9-vinylanthracene, 4-vinyl benzocyclobutene, 4-vinylbiphenyl, 2-vinylnaphthalene and 2-vinylnaphthalene, to name a few examples. The solvent may also include a crosslinking agent in addition to the vinyl-containing monomer in order to promote crosslinking after printing, or a cross-linking monomer having two or more vinyl moieties including but not limited to o-divinylbenzene, m-divinylbenzene and/or p-divinylbenzene.

When the solvent comprises a vinyl-containing monomer, a secondary post stabilization process may be optionally used. This secondary post stabilization process includes incorporating either a thermal or photo-induced free radical generator into the magnetic ink composition to crosslink the monomer in the presence of the diblock and/or triblock copolymers. The crosslinking may occur either during or after deposition. The thermal or photo-induced free radical generators may generate free radicals upon the application of heat or by exposing the printed ink to actinic radiation. Any number of known radical forming materials, such as photoinitiators, could find use in some implementations of this type of post stabilization process. Several examples of photoinitiators include, without limitation, those supplied by Ciba Specialty Chemicals (Basel, Switzerland) under the trademark Irgacure®, Darocur®.

Any number of known radical forming materials, such as thermal radical generators could find use in some implementations of this type of post stabilization process. Several examples of thermal radical generators include, but are not limited to, 4,4-Azobis(4-cyanovaleric acid), 1,1'-azobis-(cyclohexanecarbonitrile), 2,2'-azobisisobutyronitrile (AIBN), benzoyl peroxide, 2,2-bis(tert-butylperoxy)butane, 1,1-bis(tert-butylperoxy)cyclohexane, 2,5-bis-(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butylperoxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, and potassium persulfate.

When desirable, a sensitizer may also be added to the magnetic ink formulation in order to increase the absorbance of the material and by energy transfer to the photo-initiator or photo-crosslinker increase the amount of radicals generated, thereby, increasing the sensitivity of the material towards photons. Any sensitizer may be chosen from those that are known in the art. Several specific examples of sensitizers include, without limitation, UVS-1101, UVS-1221, and UVS-1331 from Kawasaki Kasei Chemicals Ltd. (Japan).

When desirable, a dye also may be added to the magnetic ink composition in order to increase the absorbance without sensitization of the material. Any dye that is added to the magnetic ink may also produce a colored material that could be more aesthetically pleasing or offer other advantages. This dye may also absorb light in the non-visible part of the spectrum and be used to reduce the amount of light penetration into the material and thus limit the depth to which crosslinking of the copolymers occurs. The advantage of limiting the depth of crosslinking would be to obtain finer resolution in the depth or Z-direction of each discrete structure or voxel.

According to yet another aspect of the present disclosure, the ink may also comprise one or more additives. These additives may include but not be limited to surfactants (e.g., non-ionic), coating property-improving agents, stabilizers, colorants, ultraviolet absorbers, antioxidants, and defoaming agents. The amount of each additive may be any level that does not impair the desired properties of the magnetic ink.

Alternatively, the additive may be added to the magnetic ink composition in an amount that is less than about 2 parts by weight per 100 parts by weight of the ink composition. Alternatively, the additive is added in an amount that ranges from about 0.005 to about 1 part by weight per 100 parts by weight of the ink composition.

Several examples of nonionic surfactants that may be used include, without limitation, polyoxyethylene alkyl ethers, such as polyoxyethylene lauryl ether, polyoxyethylene stearyl ether, and polyoxyethylene oleyl ether; polyoxyethylene alkylphenyl ethers, such as polyoxyethylene octylphenyl ether and polyoxyethylene nonylphenyl ethers; and polyethylene glycol dialkyl esters, such as polyethylene glycol dilaurate and polyethylene glycol distearate.

Alternatively, the surfactants may also include fluorine-containing surfactants that contain one or more fluoroalkyl or perfluoroalkyl groups. Several examples of fluorine-containing surfactants include, but are not limited to Efftop® EF301, EF303 and EF352 (manufactured by Shinakitakasei Co., Ltd., Japan), Megafac® F171, F172 and F173 (manufactured by Dainippon Ink Co., Ltd., Tokyo, Japan), Asahiguard® AG710 (manufactured by Asahi Glass Co., Ltd., Japan), Florade FC430 and FC431 (manufactured by Sumitomo 3M Co., Ltd., Japan), and Surflone® S-382, SC101, SC102, SC103, SC104, SC105 and SC106 (manufactured by Asahi Glass Co., Ltd., Japan).

The optional surfactant incorporated into the magnetic ink composition may also be an organosiloxane surfactant, an acrylic acid-type polymer, or methyacrylic acid-type polymer. One specific example of an organosiloxane surfactant includes KP341 (manufactured by Shinetsu Kagaku Kogyo Co., Ltd., Japan). Organosiloxane surfactants may also decrease the surface tension exhibited by the magnetic ink composition. Several examples of acrylic acid-type or methacrylic acid-type polymers and copolymers include, without limitation, Polyflow® No. 75, No. 95, and WS (manufactured by Kyoeisha Yushikagaku Kogyo Co., Ltd., Japan).

Although an advantage of the magnetic inks of the present disclosure is that high permeability can be achieved in the structures formed by directly printing and drying the ink composition without the need for post processing treatments, in certain applications post-processing treatments may be desirable and can be practiced as part of the invention. Several non-limiting examples of such post-processing treatments include thermal sintering, electrical sintering, chemical sintering, plasma sintering, photonic sintering, and microwave sintering.

According to another aspect of the present disclosure a 3-D printed device comprising one or more structures is provided that comprises a plurality of magnetically responsive particles and one or more diblock or triblock polymers as previously described above. An example of such a device is a digital phased array where advances in solid-state electronics have enabled system-on-chip designs where there is a mixture of both digital and RF functions. The integration of these components can require structures that are significantly larger that the device itself. This is especially true for impedance matching and mode transitioning structures that operate at larger percent bandwidth. Here 3-D printing would enable direct integration of the chip within the radiating elements without the need for additional interconnections. The final system will use subtractive manufacturing techniques to fabricate the gross structure and 3-D printing for the fine internal RF structures.

The magnetic ink composition may also be used for printing complex RF devices, for example, antennas. The magnetic ink composition may also be used for printing microfluidic devices that contain conductive wires where current 3-D printing of complex multilevel devices with such conductive wires is not possible. The advantages of the magnetic ink composition and the 3-D printing thereof include high resolution and permeability without need to be exposed to a post processing sintering treatment.

The compositions according to the invention can be used to fabricate materials that allow controlling propagation of electromagnetic waves, e.g., radio frequency waves. By way of example, in some embodiments, the compositions according to the present teachings can be employed to generate 3-D printed graded index low-loss materials. As shown in FIG. 1, such materials can be used in RF devices, e.g., a horn antenna, to provide enhanced impedance matching of a waveguide to free space. FIG. 1 shows an RF waveguide that is coupled at its output aperture to an RF horn antenna. The waveguide can be characterized by a complex impedance $\eta_w$, which is different than the impedance of the free space $\eta_o$ into which the radiation from the waveguide is transmitted. Traditionally, a flared horn antenna is coupled to the output aperture of the waveguide so as to provide a transition region exhibiting a gradual change in impedance from the output aperture of the waveguide to free space so as to optimize coupling of the radiation from the waveguide to free space.

In some embodiments, magnetic materials according to the present teachings can be employed to form graded-index lenses or inserts that can be coupled to an RF horn antenna to improve its impedance-matching properties. Alternatively, as shown in FIG. 1, the horn antenna itself can be formed of a graded-index material to form a transition region according to the present teachings.

A 3-D printing extrusion device is an example of a device that can be utilized to fabricate 3-D print graded index low-loss materials according to the present teachings, i.e., materials that exhibit spatial variation of electric permittivity and magnetic permeability.

Examples of inks with varied relative permittivity are shown below to illustrate this concept though the same concept can be used to describe other properties such as permeability. Examples of printed dielectrics that can be fabricated using varied compositions according to the present teachings are shown in Table 1 below:

TABLE 1

Exemplary 3-D Printer Dielectrics

| Material (vol. %) | Relative Permittivity (ε') (34 GHz) | Loss Tangent (ε"/ε') (34 GHz) |
|---|---|---|
| SIS Polymer | 2.2 | 0.002 |
| Al$_2$O$_3$/SIS (45:55) | 4.1 | 0.003 |
| TiO$_2$/SIS (45:55) | 9.9 | 0.016 |
| SrTiO$_3$/SIS (45:55) | 16.0 | 0.033 |

The theoretical permittivity E of the exemplary compositions can be calculated by the following equation:

$$\varepsilon = \varepsilon_B \left[ 1 + \frac{f_A(\varepsilon_A - \varepsilon_B)}{\xi_B + n(1 - f_A)(\varepsilon_A - \varepsilon_B)} \right]$$

where $\varepsilon_A$ is the permittivity of the filler and $\varepsilon_B$ is the permittivity of the polymer, $f_A$ is the fill ratio (volume fraction of filler) and $\eta$ is a scaling factor based on the sphericity of the filler nanoparticles.

Figure 2:
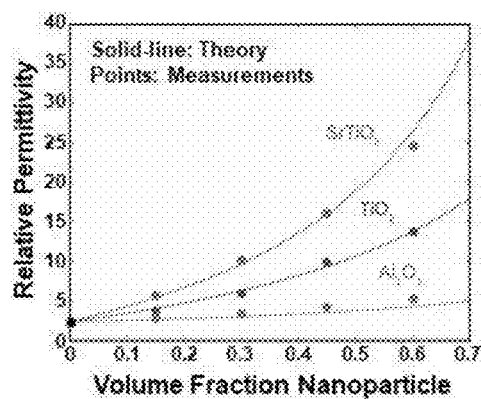
FIG. 2 is a graph showing the relative permittivity of various materials according to the invention as a function of the volume fraction of nanoparticles in the composition.

FIG. 2 shows excellent agreement between the theoretical and actually measured permittivities of the exemplary compositions of Table 1 at various fill fractions. The graphs presented in FIG. 2 provide examples of variation of relative permittivity of a magnetic composition comprising SIS polymer (Polystyrene-block-polyisoprene-block-polystyrene (SIS) (432415) purchased from Sigma-Aldrich, St. Louis, MO) in which a plurality of different particles are dispersed as a function of volume fraction of three different particles dispersed within the composition. The graphs show that the relative permittivity increases as the volume fraction of the particles dispersed in the polymer increases, albeit with different rates of increase for the different particles employed in this example.

In some embodiments, the teachings of the present invention can be employed to fabricate materials that exhibit a spatial variation of relative permittivity. For example, graded-index lenses can be formed of a magnetic material according to the present teachings. The dielectric filler fraction and, hence the index of refraction of the lens can vary as a function x, y, and z. For example, the dielectric fraction can decrease from center to edge, or can increase from center to edge to enhance RF device fabrication capabilities, and it should be understood that compositions according to the present teachings can be 3-D printed to form a variety of different graded indices of refraction. Further, the graded-index lens can be employed for application other than RF.

Figure 3:
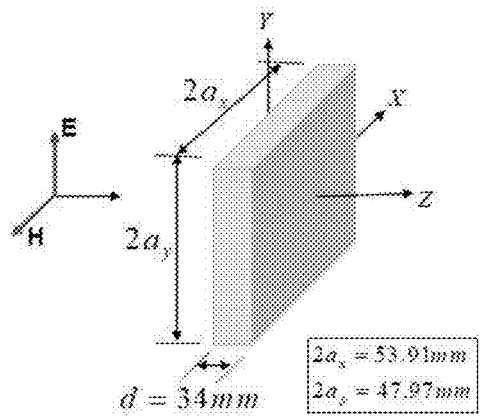
FIG. 3 is a schematic illustration of a flat GRIN lens according to the invention.

FIG. 3 provides a schematic illustration of a flat graded-index (GRIN) lens.

Figure 4:
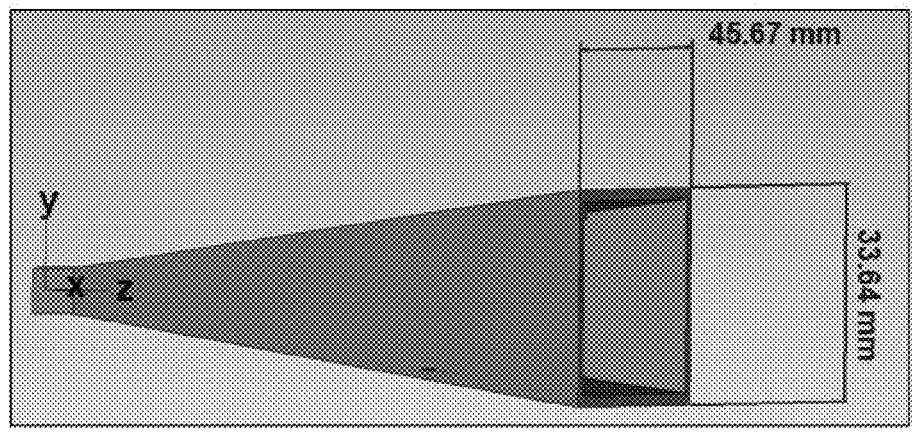
FIG. 4 illustrates a conventional horn antenna with the depicted dimensions.
Figure 4A:
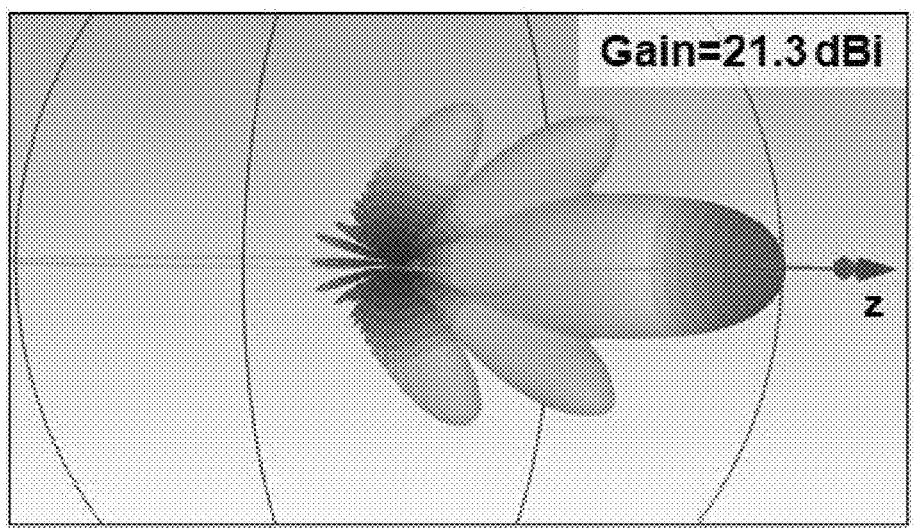
FIG. 4A provides a simulated illustration of the calculated gain profile of the horn antenna of FIG. 4.

FIG. 4 illustrates a conventional horn antenna with the depicted dimensions. and FIG. 4A provides a simulated illustration of the calculated gain profile of this conventional horn antenna. The darker areas represent areas of higher signal from the antenna feed point.

Figure 5:
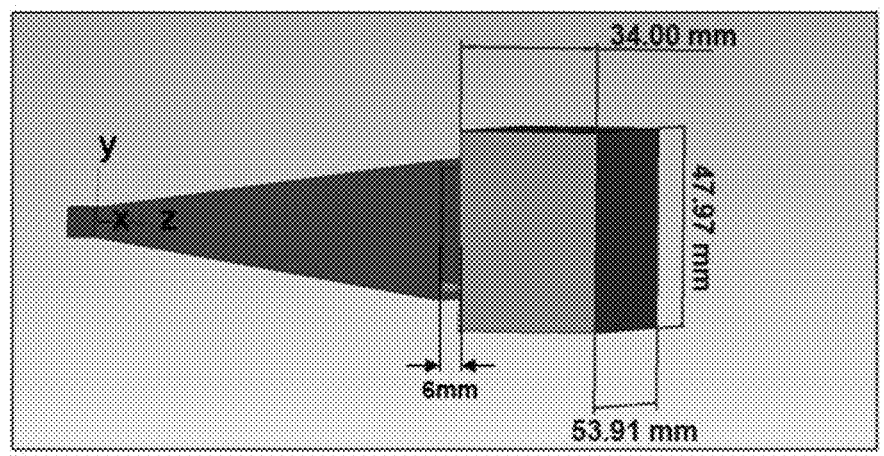
FIG. 5 illustrates a horn antenna with an output aperture that is coupled to a graded-index lens according to the present teachings, such as the graded-index lens illustrated in FIG. 3.
Figure 5A:
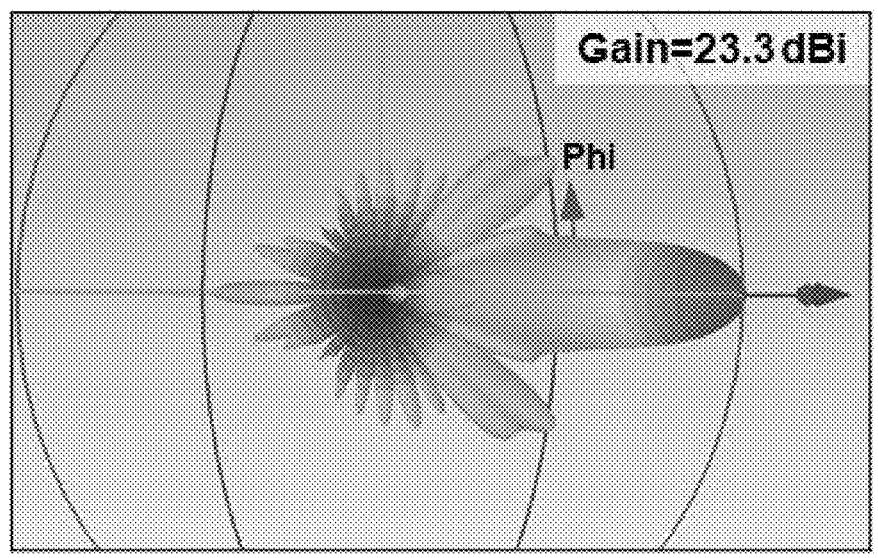
FIG. 5A shows the calculated gain profile of the horn antenna and the lens.

FIG. 5 illustrates a horn antenna with an output aperture that is coupled to a graded-index lens according to the present teachings. FIG. 5A shows the calculated gain profile of the horn antenna and the lens. A comparison of the grain profiles of FIGS. 4A and 5A shows that the coupling of the graded-index lens to the horn antenna improves the gain of the horn antenna and further provides a narrower beam. It is also worth noting that the initial reflection of the beam increases at the surface of the GRIN lens. By introducing permeable particles into the lens as well this reflection would be further reduced by better impedance matching to the free wave. For simplicity this was not included in the shown example.

Figure 6:
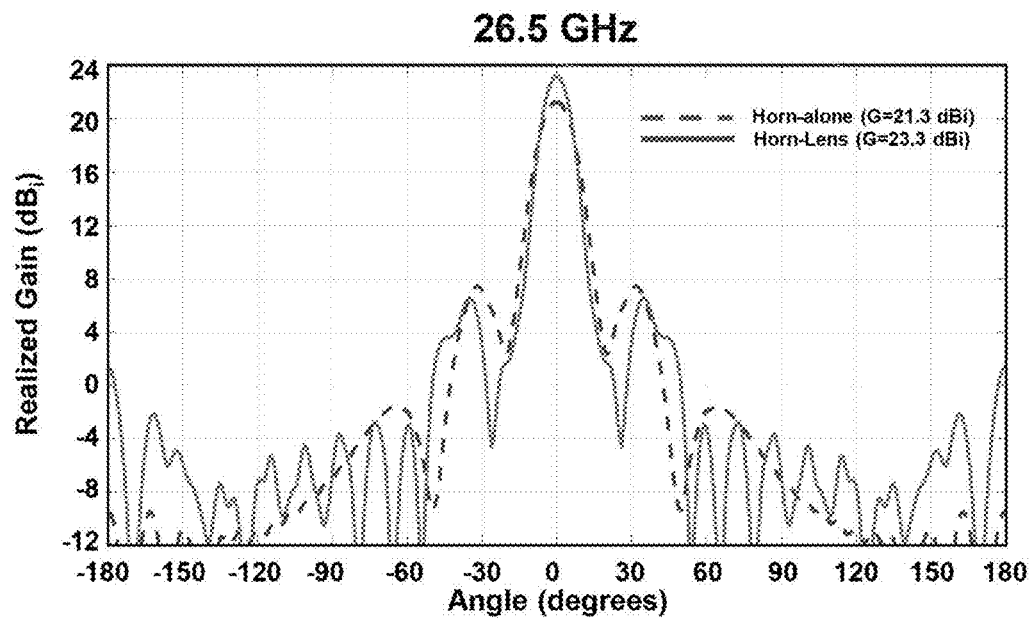
FIG. 6 is a graph of the simulated gain of the above RF horn antennas, i.e., without and with a graded-index lens, as a function of angle.

FIG. 6 is a graph of the simulated gain of the above RF horn antennas, i.e., without and with a graded-index lens, as a function of angle. FIG. 6 and the accompanying Table 2 show that the coupling of the graded-index lens to the horn antenna enhances the maximum gain of the antenna, i.e., gain at zero emission angle, and further results in narrowing of the main emission lobe of the antenna.

TABLE 2

| | Realized Gain (dBi) | | | HPWB (E-plane) | | | HPWB (H-plane) | | | Front/Back Ratio (dB) | | |
|---|---|---|---|---|---|---|---|---|---|---|---|---|
| Frequency (GHz) | 26.5 | 33.25 | 40 | 26.5 | 33.25 | 40 | 26.5 | 33.25 | 40 | 26.5 | 33.25 | 40 |
| Horn antenna | 21.3 | 24 | 26.2 | 14.6° | 10.7° | 8.2° | 15.4° | 11.8° | 9° | 30.71 | 35.7 | 29.02 |
| Horn antenna and lens | 23.3 | 24.5 | 26.6 | 11.2° | 8.3° | 6.6° | 12.2° | 9.8° | 7.1° | 21.85 | 15.07 | 22.24 |

Figure 7:
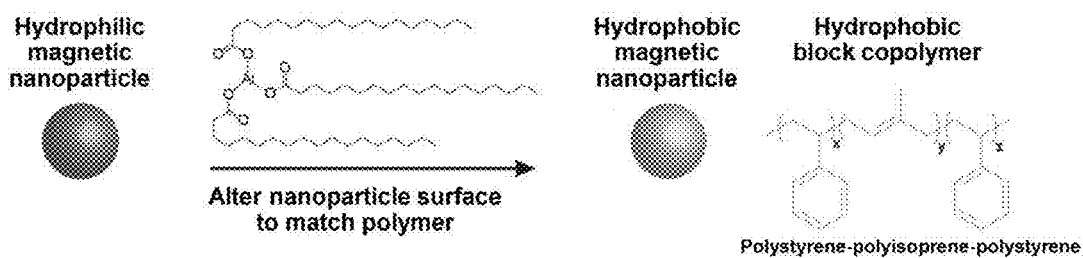
FIG. 7 schematically illustrates one embodiment of a method for generating a magnetic composition according to the disclosures herein.

FIG. 7 schematically depicts steps of a method for generating a magnetic composition according to an embodiment. In this embodiment, the surfaces of a plurality of magnetic nanoparticles are modified so as to render the particles hydrophobic. In this embodiment, the surface-modifying agent (aluminum stearate) forms a bond with the nanoparticles surfaces so as to coat the particles. Polystyrene-polyisoprene-polystyrene hydrophobic block copolymer and the surface-modified nanoparticles are combined in a volatile, organic solvent.

Figure 8:
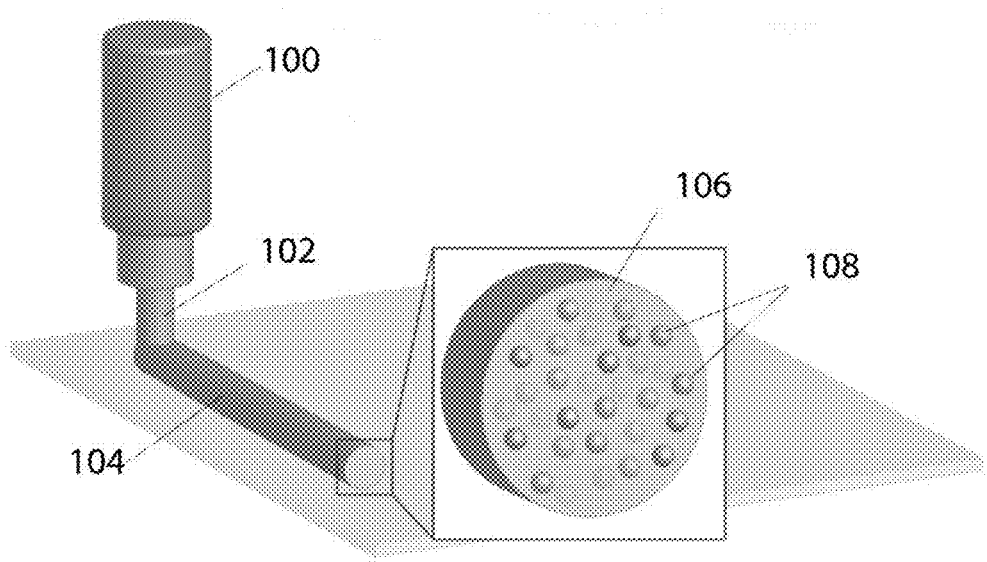
FIG. 8 is a schematic illustration of a printing nozzle and the resulting printed composition of magnetically responsive particles in a polymeric matrix according to the disclosures.

FIG. 8 illustrates a printing apparatus and method according to the disclosure. The apparatus comprises a printing head 100 with an extrusion nozzle 102 that prints an ink 104 that comprises one or more magnetically responsive particles, a block copolymer, and a solvent. The solvent rapidly evaporates as the magnetic composition is extruded via the printing head 100 to generate a magnetic material of interest 104 that comprises magnetic particles 108 within a polymeric matrix 106. Further details on printing apparatus and methods can be found, for example, in U.S. Patent Application Pub. No. 2016/0346997 entitled "Three Dimensional (3D) Printed Composite Structure and 3D printable Composite Ink Formulation," hereby incorporated by reference in its entirety. The apparatus and method can be used to produce various magnetically responsive devices, such as the above described graded-index lenses.

EXAMPLES

A number of exemplary magnetic ink compositions are described below in Table 3. The polymeric component in each instance was Polystyrene-block-polyisoprene-block-polystyrene (SIS) (432415) (Sigma-Aldrich, St. Louis, MO). The magnetic inks containing iron carbonyl were formulated with generally spherical iron carbonyl particles with diameters of 1-3 microns obtained from Fisher Scientific (Pittsburgh, PA, USA). (For further composition details, see, https://www.fishersci.com/shop/products/iron-powder-spherical-1-3-micron-98-alfa-aesar-4/AA4033714 for further details). The particles were surface-functionalized with aluminum stearate via a solution-based reaction. In brief, 50 g of particles and 2.5 g of aluminum stearate were combined with 500 mL of toluene in a round bottom flask. Reaction was stirred at reflux for 2 days and the modified particles were then separated via centrifugation.

The surface-functionalized iron carbonyl particles are designated SM-IC.

The magnetic inks containing yttrium iron garnet (YIG) were roughly the same diameter and obtained from Skyworks Solutions, Inc. (Irvine, CA, USA). (See, for example, http://www.skyworksinc.com/Product/3492/G-1200?IsProduct=true.) The YIG particles were surface-modified in the same manner as the iron carbonyl particles. The surface-functionalized YAG particles are designated SM-YAG. Further details on the magnetic properties of iron garnets can be found in IEEE Transactions on Magnetics, Vol. 37, No. 4, July 2001, pp 2445-2447, herein incorporated by reference in its entirety.

The examples presented in Table 3 are given to illustrate the magnetic ink compositions, formed according to the invention, as well as the methods of printing and resulting products should not be construed to limit the scope of the disclosure. Printable inks were created by combining polymer, nanoparticles and solvent in an AR-100 planetary centrifugal mixer (Thinky USA, Laguna Hills, CA). The polymer and nanoparticles were combined in a 20 mL glass vial. Solvent was then added and the inks were loaded into the mixer and spun at 2200 RPM for 20 minutes. If a homogeneous ink was not obtained, the ink was hand mixed to disperse inhomogeneities followed by an additional cycle in the planetary centrifugal mixer at 2200 RPM for 20 minutes. This mixing cycle was repeated until homogeneous ink was obtained. The printing ink formulations showing materials and material ratios by mass are presented in Table 3 below.

TABLE 3

Printing ink formulations.

| Ink ID # | Polymer | Parts | Particle | Parts | Solvent | Parts |
|---|---|---|---|---|---|---|
| YIG-1 | SIS | 30.7 | SM-YIG | 30.4 | Toluene | 38.9 |
| YIG-2 | SIS | 21.6 | SM-YIG | 51.8 | Toluene | 26.6 |
| YIG-3 | SIS | 14.4 | SM-YIG | 65.6 | Toluene | 20.0 |
| YIG-4 | SIS | 8.7 | SM-YIG | 73.3 | Toluene | 18.0 |
| IC-1 | SIS | 27.8 | SM-IC | 40.6 | Toluene | 31.5 |
| IC-2 | SIS | 16.9 | SM-IC | 59.8 | Toluene | 23.3 |
| IC-3 | SIS | 10.8 | SM-IC | 72.8 | Toluene | 16.4 |
| IC-4 | SIS | 7.0 | SM-IC | 86.2 | Toluene | 6.8 |

Those skilled-in-the-art, in light of the present disclosure, will appreciate that changes can be made in the specific embodiments which are disclosed herein and still obtain alike or similar results without departing from or exceeding the spirit or scope of the disclosure. The skilled artisan will further understand that any properties reported herein represent properties that are routinely measured and can be obtained by multiple different methods. The methods described herein represent one approach and other methods may be utilized without exceeding the scope of the present disclosure.

Within this specification, embodiments have been described in a way that enables a clear and concise specification to be written, but it is intended and will be appreciated that embodiments may be variously combined or separated without departing from the invention. For example, it will be appreciated that all preferred features described are applicable to all aspects of the invention described herein. All patents, patent applications and publications of any kind cited in this specification are herein incorporated in their entirety by reference.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A 3-D printed device, comprising a structure formed by a plurality of magnetically responsive particles and one or more diblock or triblock copolymers; the diblock or triblock copolymers having an A-B, A-B-A, or A-B-C block-type structure in which the A-blocks and C-blocks are an aromatic-based polymer or an acrylate-based polymer and the B-blocks are an aliphatic-based polymer; wherein at least a portion of the structure exhibits a magnetic permeability greater than about $1.3 \times 10^{-6}$ H/m; wherein a concentration of the magnetically responsive particles varies in different portions of the structure; wherein at least a portion of the 3-D printed device comprises a structure in which the concentration of magnetically responsive particles varies according to a gradient; wherein the 3D printed device is a radio frequency (RF) antenna.

2. The 3-D printed device of claim 1, wherein the 3-D printed device is a graded index device.

3. The 3-D printed device of claim 1, wherein the 3-D printed device is a lens for coupling to an RF antenna or RF horn antenna.

4. The 3-D printed device of claim 1, wherein the structure is formed by a magnetic ink composition, the magnetic ink composition comprising a plurality of magnetically responsive particles and one or more diblock or triblock copolymers; the diblock or triblock copolymers having an A-B, A-B-A, or A-B-C block-type structure in which the A-blocks and C-blocks are an aromatic-based polymer or an acrylate-based polymer and the B-blocks are an aliphatic-based polymer; wherein the magnetic particles comprise 0.5 wt. % to 40 wt. % of at least a portion of the structure based on the dry weight of the magnetic ink composition; wherein at least a portion of the structure exhibits a magnetic permeability greater than about $1.3 \times 10^{-6}$ H/m.

5. The 3-D printed device of claim 1, wherein the 3-D printed device is a graded index device, wherein the structure exhibits different variations in the concentration of the magnetically responsive particles.

6. The 3-D printed device of claim 1, wherein the magnetically responsive particles have a surface that is modified.

7. The 3-D printed device of claim 6, wherein the wherein the surface is modified with one or more of: a surfactant; a hydrophobic moiety; a polyvinylpyrrolidone; an amine-containing compound; or a silane coupling agent.

8. The 3-D printed device of claim 1, wherein the structure further comprises dielectric particles having an electrical permittivity different from an electrical permittivity of the magnetically responsive particles.

9. The 3-D printed device of claim 8, wherein a concentration of the dielectric particles varies in different portions of the structure.

10. The 3-D printed device of claim 8, wherein a concentration of the dielectric particles and a concentration of the magnetically responsive particles vary in different parts of the structure.

11. The 3-D printed device of claim 8, wherein the 3-D printed device is a graded index device, wherein the structure exhibits different ratios of the concentration of dielectric particles and the concentration of magnetically responsive particles.

* * * * *